(12) United States Patent
McCormick (10) Patent No.: US 12,011,150 B2
(45) Date of Patent: Jun. 18, 2024

(54) RADIOLUCENT RETRACTOR

(71) Applicant: Eric McCormick, Noblesville, IN (US)

(72) Inventor: Eric McCormick, Noblesville, IN (US)

( * ) Notice: Subject to any disclaimer, the term of this patent is extended or adjusted under 35 U.S.C. 154(b) by 997 days.

(21) Appl. No.: 16/906,338

(22) Filed: Jun. 19, 2020

(65) Prior Publication Data
US 2021/0068800 A1 Mar. 11, 2021

Related U.S. Application Data

(63) Continuation-in-part of application No. 16/126,177, filed on Sep. 10, 2018, now abandoned.

(51) Int. Cl.
| | |
|---|---|
| *A61B 17/02* | (2006.01) |
| *A61L 2/20* | (2006.01) |
| *A61B 17/00* | (2006.01) |
| *A61L 101/44* | (2006.01) |

(52) U.S. Cl.
CPC .......... *A61B 17/0206* (2013.01); *A61L 2/206* (2013.01); *A61B 2017/0023* (2013.01); *A61B 2017/00738* (2013.01); *A61B 2017/00889* (2013.01); *A61B 2017/0092* (2013.01); *A61B 2017/00955* (2013.01); *A61L 2101/44* (2020.08); *A61L 2202/24* (2013.01)

(58) Field of Classification Search
CPC ........ A61B 17/0206; A61B 2017/0023; A61B 2017/00738; A61B 2017/00889; A61B 2017/0092; A61B 2017/00955; A61L 2/206; A61L 2101/44; A61L 2202/24
USPC ................................................. 600/219, 224
See application file for complete search history.

(56) References Cited

U.S. PATENT DOCUMENTS

| | | | | |
|---|---|---|---|---|
| 1,194,319 | A * | 8/1916 | Pretts ...................... | A61B 1/32 600/224 |
| 3,038,467 | A * | 6/1962 | Sovatkin ............ | A61B 17/0206 600/219 |
| 3,840,014 | A | 10/1974 | Ling | |
| 5,174,278 | A * | 12/1992 | Babkow .................... | A61B 1/32 600/210 |
| 5,299,563 | A * | 4/1994 | Seton ................. | A61B 17/0293 600/215 |
| 6,102,852 | A | 8/2000 | Liu | |

(Continued)

*Primary Examiner* — Tessa M Matthews
*Assistant Examiner* — David C Comstock
(74) *Attorney, Agent, or Firm* — David E. Novak; Brannon Sowers & Cracraft PC (57) ABSTRACT

A disposable device for tissue retraction, including first and second elongated curved members, each having respective proximal and distal ends, a hinge pivotably connecting first and second elongated curved members, wherein first and second curved members curve away from one another, a first blade extending from the distal end of the first elongated curved member, and a second blade extending from the distal end of the second elongated curved member. The device further includes a first latching portion extending from the proximal end of the first elongated curved member, a second latching portion extending from the proximal end of the second elongated curved member, and a third bladed elongated member lockingly engageable to the hinge. The first and second latching portions are lockingly engageable. The retractor is made of a generally electrically insulating nonmagnetic radiolucent material.

12 Claims, 9 Drawing Sheets

(56) References Cited

U.S. PATENT DOCUMENTS

| | | | |
|---|---|---|---|
| 6,196,969 B1* | 3/2001 | Bester | A61B 17/0206 |
| | | | 600/219 |
| 6,544,169 B2 | 4/2003 | Putrino | |
| 8,257,256 B1 | 9/2012 | Krolman | |
| 8,376,939 B1 | 2/2013 | Leyva | |
| 8,899,809 B2 | 12/2014 | Vayser | |
| 9,468,405 B2* | 10/2016 | Miles | A61B 17/0206 |
| 2003/0055320 A1* | 3/2003 | McBride | A61B 17/0206 |
| | | | 600/217 |
| 2005/0027170 A1 | 2/2005 | Nohara | |
| 2005/0080320 A1* | 4/2005 | Lee | A61B 17/0293 |
| | | | 600/214 |
| 2005/0215865 A1 | 9/2005 | LeVahn | |
| 2011/0046450 A1 | 2/2011 | Blaine | |
| 2011/0060194 A1 | 3/2011 | Risto | |
| 2011/0105849 A1 | 5/2011 | Covello | |
| 2012/0130180 A1 | 5/2012 | Pell | |
| 2015/0209022 A1 | 7/2015 | Ruppert | |
| 2017/0311942 A1* | 11/2017 | Daavettila | A61B 17/0206 |
| 2017/0333023 A1* | 11/2017 | Adams | A61B 17/0206 |
| 2018/0353164 A1* | 12/2018 | Laird, Jr. | A61B 17/2812 |

* cited by examiner

RADIOLUCENT RETRACTOR

BACKGROUND

During surgery, the surgeon must be able to both see what he is doing as well as to have sufficient room to maneuver. Retractors are devices commonly used to pull tissue away from the operative area to allow the surgeon room and visibility. Retractor devices allow access to otherwise concealed tissues and surrounding areas, and are useful in both general surgery as well as microsurgical procedures.

Most retractors are made of metal, allowing for multiple uses and are typically disinfected by means of autoclaving. However, metal retractors have the disadvantage of being radiopaque. In many microsurgical procedures, there is insufficient room available for the surgeon to completely visually observe the operative area, especially from all relevant angles, and x-ray or like penetrating imaging is used in real time to guide the surgeon. Such imaging is difficult to perform when multiple surgical tools, including stationary metal retractors, are in use during the operation.

Another drawback of most retractors is that they must be manually held in place during the operation. Such requisite manpower adds to the cost of surgery as well as crowding the operating venue.

Thus, there remains a need for an improved retractor. The present invention addresses this need.

DETAILED DESCRIPTION

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

The present novel technology relates to a single use or 'disposable' device 10 for holding tissues away from a field of operation, such as by pushing open the edges of a wound to allow access thereinto. The device 10 is electrically insulating, non-magnetic, and radiotransparent, and is typically a unitary, homogeneous body molded or printed from a (typically) medical grade thermoplastic resin or like material, and is typically nonporous. The device includes a pair of elongated legs 15 extending from a transverse portion 20 to define a generally wishbone-shaped retractor 10. A tissue-engaging plate portion 25 is typically positioned at the terminal end (opposite the transverse portion 20) of each leg 15 for engaging and urging tissue away from a wound or incision. The plate 25 may further include a plurality of tissue-gripping fingers 30 extending away from the leg 15. The fingers 30 may be straight or curved to better engage the tissue. Curved fingers 30 typically curve away from the retractor 10. In some embodiments, the fingers 30 may curl into hooks to even better grip tissue.

Figure 1:
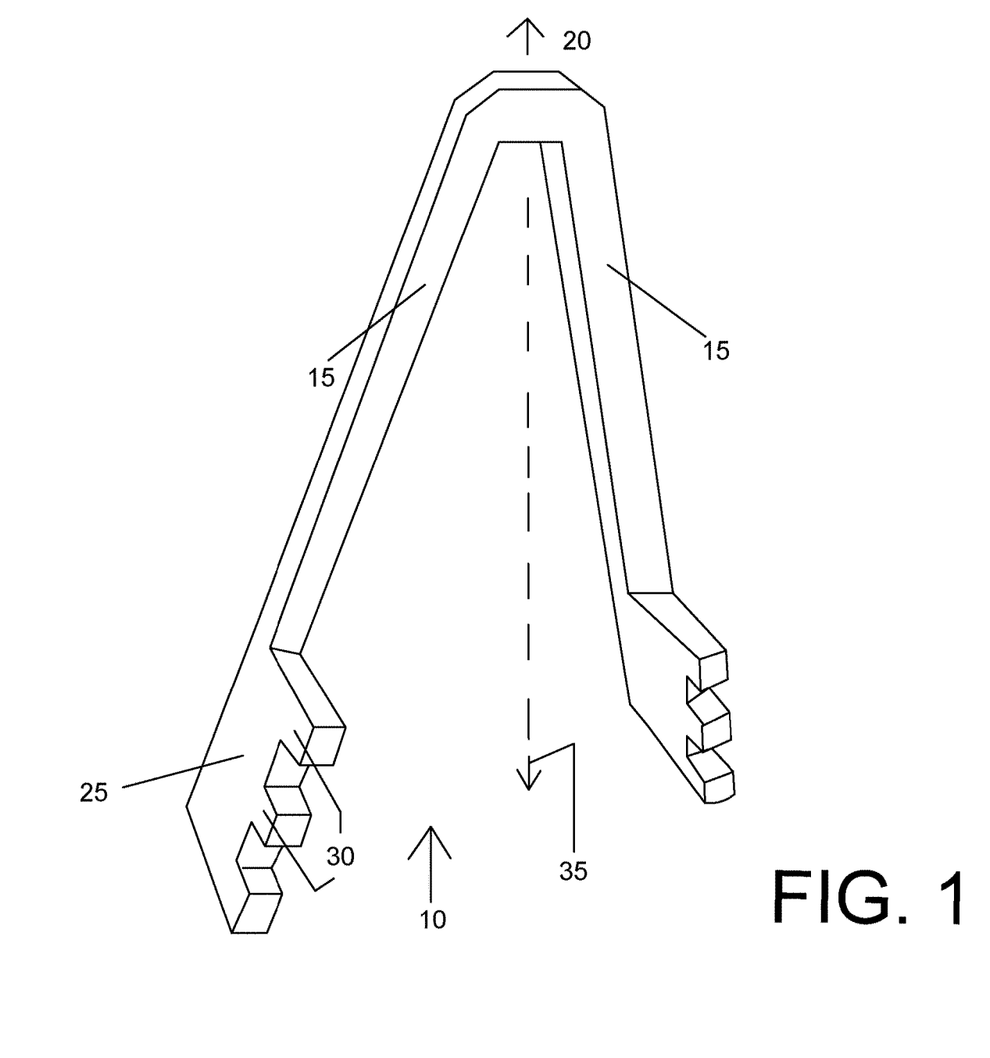
FIG. 1 is a first perspective view of a retractor device according to a first embodiment of the novel technology.
Figure 2:
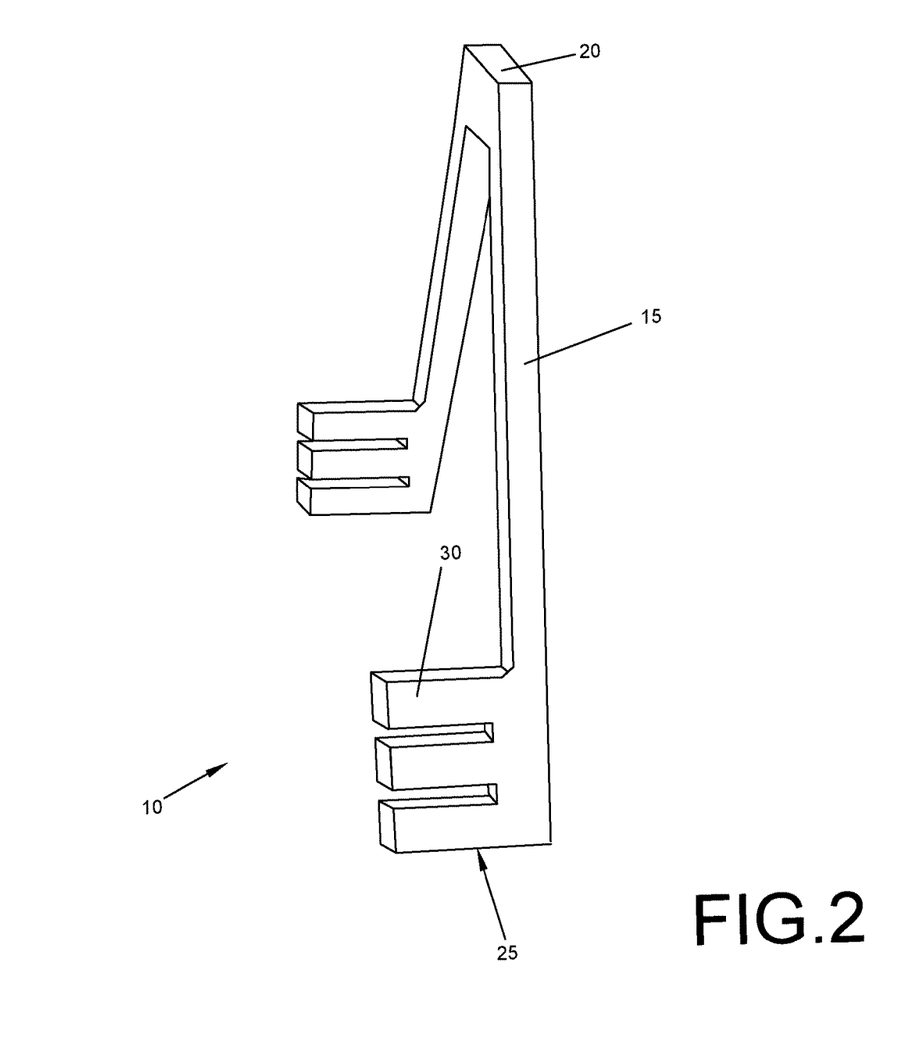
FIG. 2 is a second perspective view of the embodiment of FIG. 1.
Figure 3:
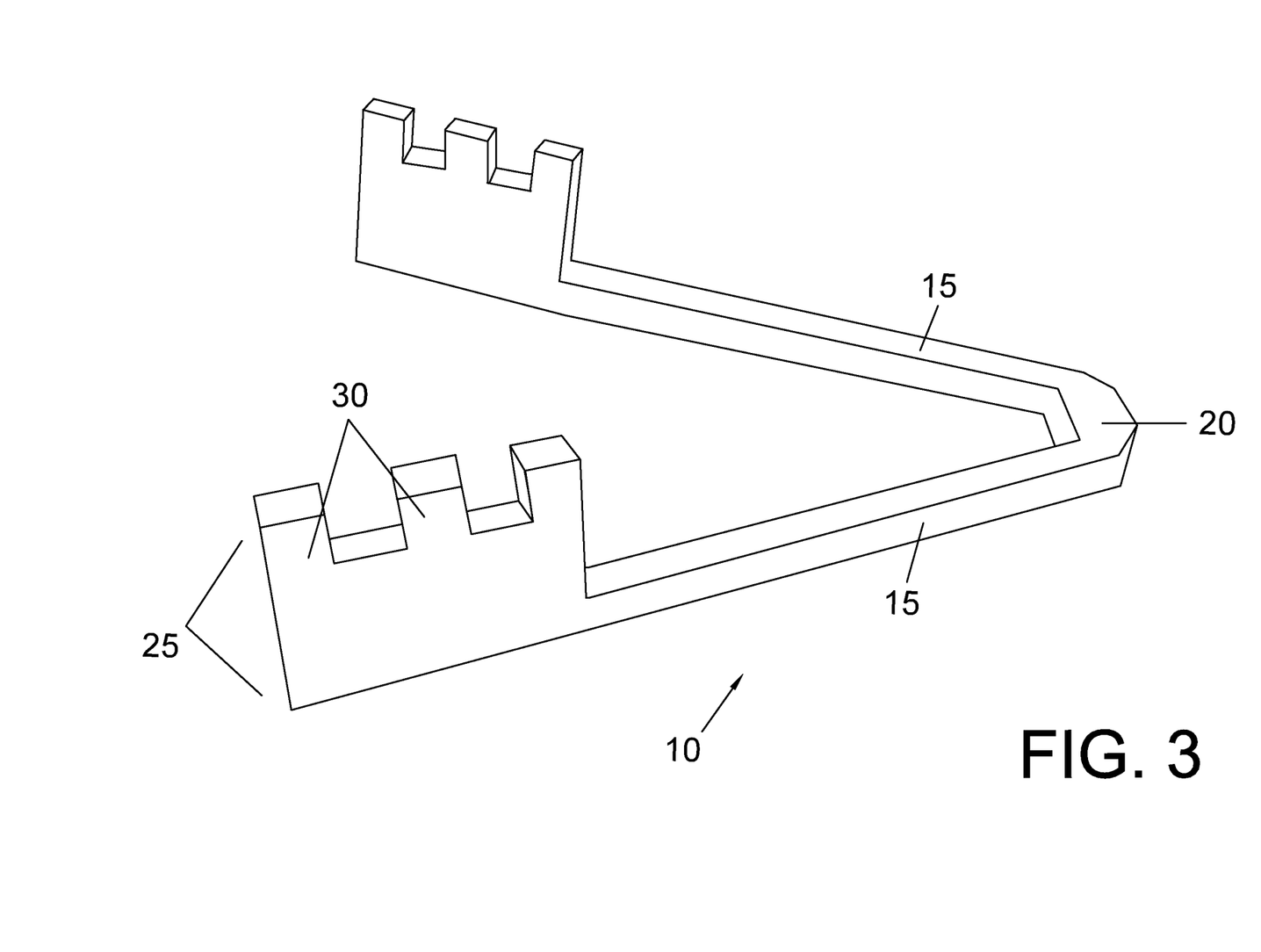
FIG. 3 is a third perspective side view of the embodiment of FIG. 1.

In one embodiment, each leg is about 8 cm. in length and has a generally square cross section of 8 mm. on a side. The transverse portion is about 1.5 cm. long. The legs 15 are not parallel, and typically each leg 15 extends away from the other leg 15 with the plates 25 being spaced about 6 cm. away from one another, thus defining an angle between fifteen and sixty degrees, more typically between thirty and forty-five degrees, and still more typically about thirty-five degrees. In other words, each leg 15 extends away from a major axis 35, defined as bisecting the transverse portion 20 and lying in the same plane as the legs 15, at an angle of about seventeen and a half degrees. When pressed together, the legs 15 typically exert a force of about between about twenty-five and about fifty Newtons, more typically about thirty-five Newtons, away from one another, with each leg typically exerting a force of about between about ten and twenty Newtons, more typically about fifteen Newtons, against the edge of the wound or incision. The device 10 thus is described by a spring constant 'k' of between about 400 and about 850 N/m, more typically about 600 N/m.

The retractor 10 functions as an elongated transverse leaf spring, insofar as the legs 15, when pushed together, exert an urging force to return them to their original resting orientation. The force exerted by the legs 15 may be varied by varying the thickness of the legs 15 and transverse piece 20, the length of the legs 15, the thickness of the legs 15, the angle defined by the legs 15, and/or the composition of the retractor 10.

Prior to use, each retractor 10 is typically sterilized, such as via immersion in an ethylene oxide bath.

Figure 4:
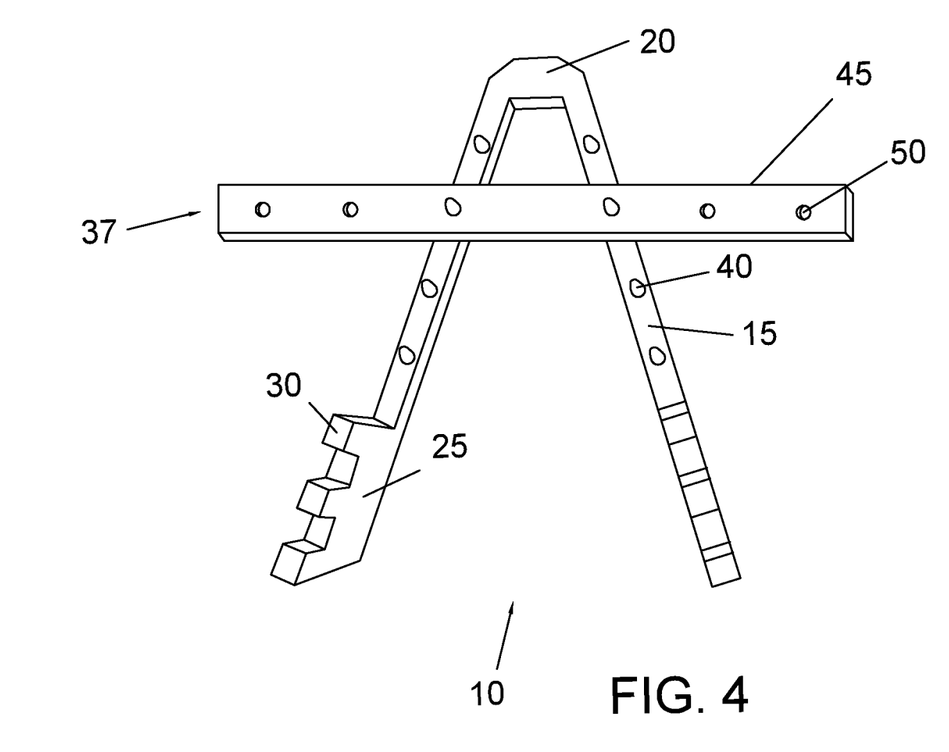
FIG. 4 is a fourth perspective view of the embodiment of FIG. 1 and including a locking device.
Figure 5:
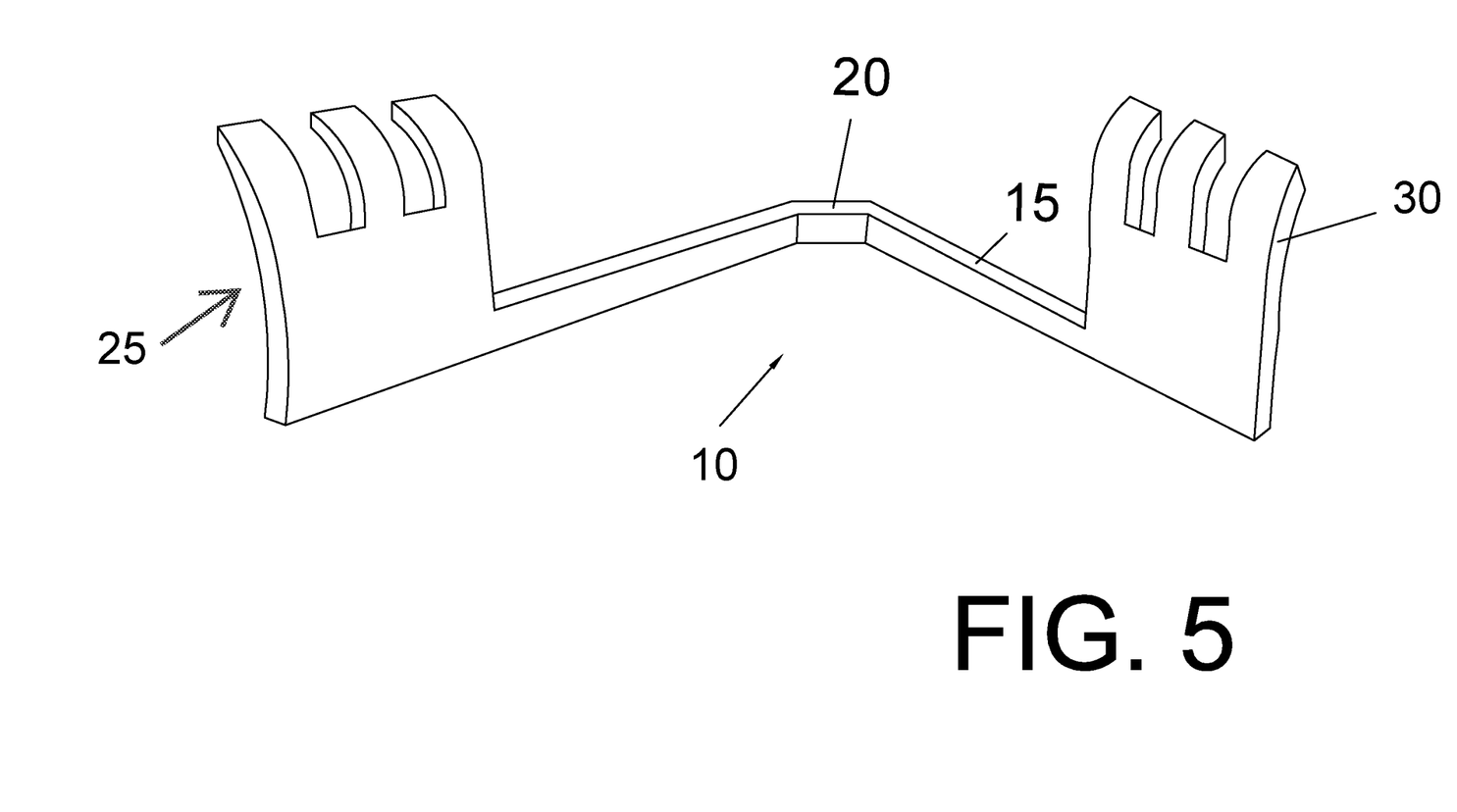
FIG. 5 is a perspective view of the embodiment of FIG. 1 but with curved fingers.

In some embodiments, the legs 15 each include a locking device 37 for preventing the legs 15 from moving relative to one another. One exemplary locking device 37 includes a plurality of spaced raised nubs or bullets 40 positioned on each leg 15, that cooperate with an elongated locking strip or latch 45 having a plurality of spaced apertures formed therethrough 50, each aperture 50 sized to snugly engage a bullet 40. The locking strip 45 may be engaged to a bullet 40 extending from each leg 15 to secure the retractor 10 once it is engaged with a patient to prevent unwanted expansion or constriction of the retractor legs 15 to control and maintain the dimensions of an incision opening.

Figure 6:
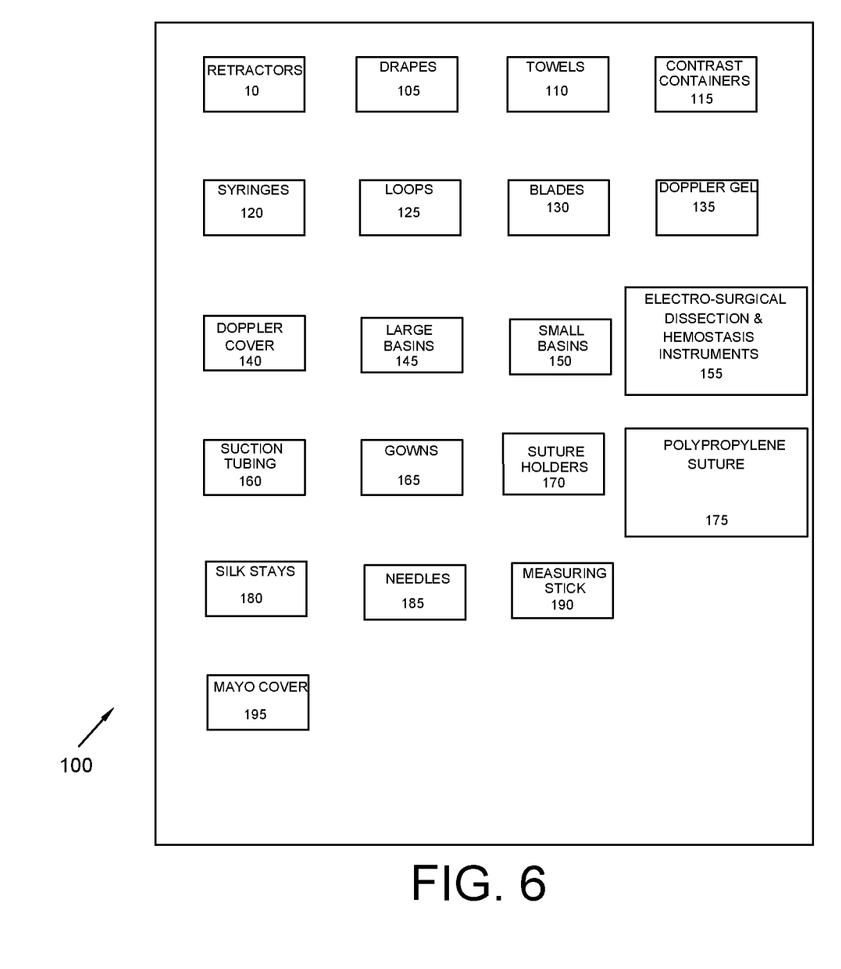
FIG. 6 is a top plan view of a second embodiment of the present novel technology, a surgical kit including the retractor embodiment of FIG. 1.

In some embodiments, the retractor 10 is included as part of a kit 100. Kit 100 typically includes at least one or more (typically a plurality) of each of the following: retractors 10, drapes 105, towels 110, contrast containers 115, syringes 120, and loops 125. Each kit 100 may also include one or more of the following: blade (typically no. 20) 130, Doppler gel 135, Doppler cover 140, large basin 145, small basin 150, electrosurgical dissection and hemostasis instrument 155, suction tubing 160, gown 165, suture holder 170, 6-0 polypropylene suture 175, 2-0 silk stays 180, needles 185, measuring stick 190, and/or mayo cover 195.

In operation, the legs 15 are first pressed together and are inserted far enough into the wound or incision such that the plates 25 and/or fingers 30 engage tissue on either side of the wound. The pressure holding the legs 15 together is then released to allow the legs 15 to exert a spring force against the tissue, urging the wound open. The retractor 10 may then be left in place to hold the wound open, and may optionally be locked by engaging the strip 45 with bullets 40 on either leg 15. Once the wound is no longer desired to be held open, the legs 15 are once again urged toward one another and the retractor 10 is removed from the wound. X-rays made during the procedure will not be impeded or obstructed by the plastic retractor, making the retractor attractive for procedures on the carotid, thrombectomies, embolectomies, pacemaker implantation, and the like.

Figure 7:
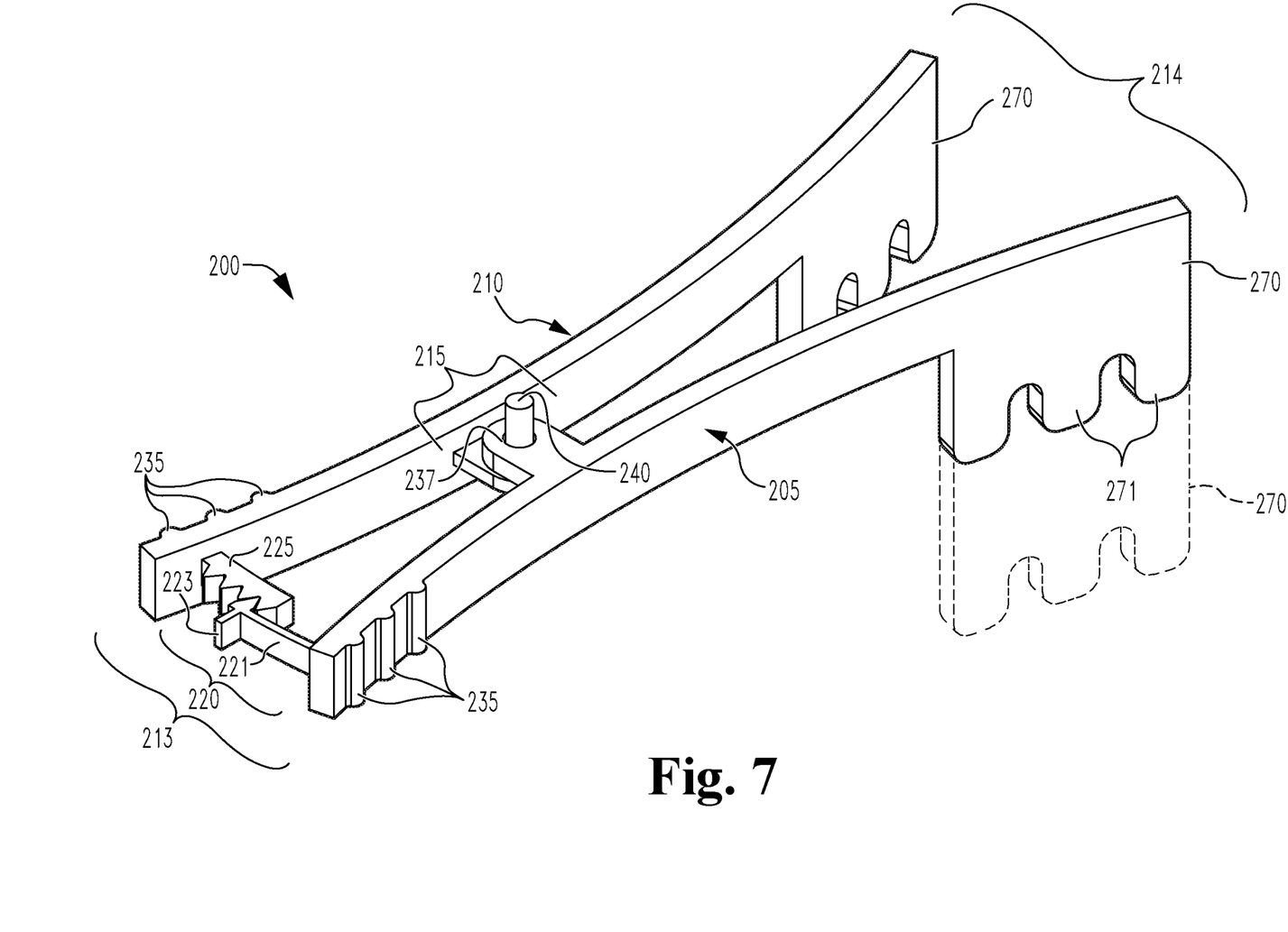
FIG. 7 is perspective view of a third embodiment retractor of the present novel technology.
Figure 8:
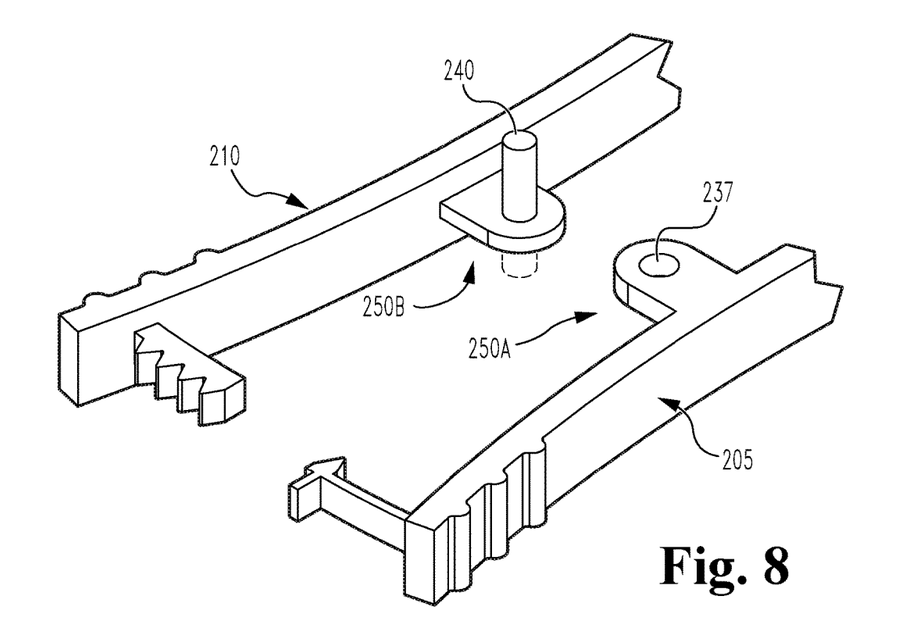
FIG. 8 is a partial perspective view of an alternate hinge assembly for use in FIG. 7.

In one embodiment, the retractor 200 includes a first prong 205 and a second prong 210 that are pivotably interconnected by a hinge assembly 215. Prongs 205, 210 are elongated members that are curved so as to provide an urging force. The prongs 205, 210 are coupled together and oriented to curve away from each other so as to provide an urging force away from one another 205, 210 when engaged to hold a wound or incision open.

Figure 9:
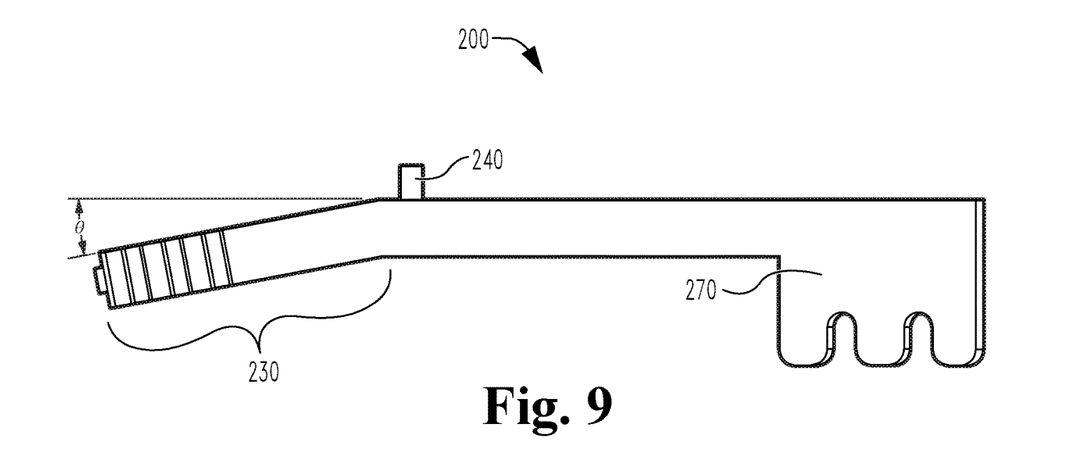
FIG. 9 is a side elevation view of FIG. 7.
Figure 10A:
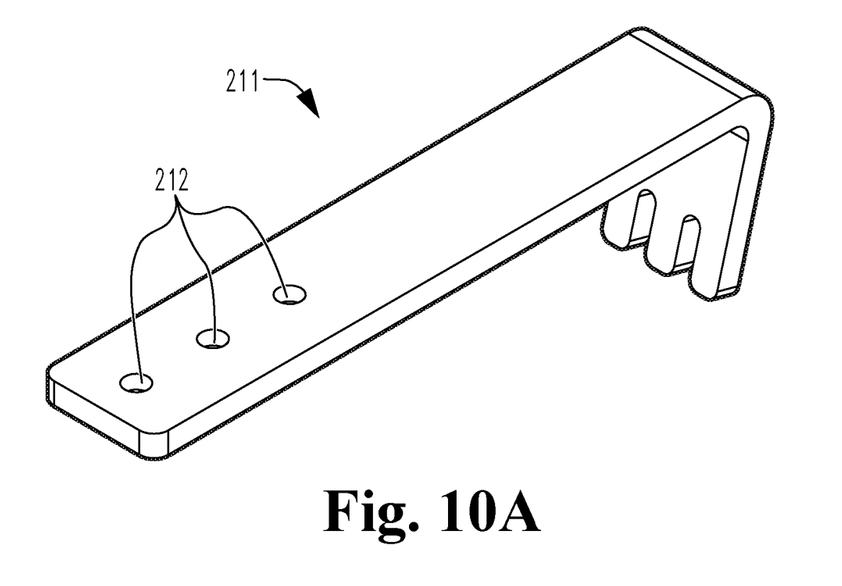
FIG. 10A is a perspective view of a center retractor member attachment for the embodiment of FIG. 7.
Figure 10B:
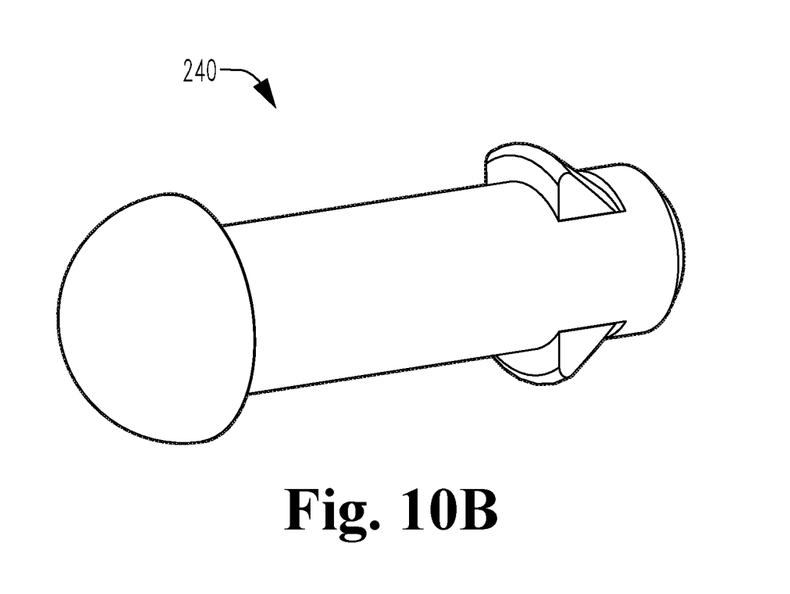
FIG. 10B is a side elevation view of a hinge pin for use with the embodiment of FIG. 7.

This embodiment retractor 200 also includes an elongated center retractor member 211 which may be connected to the retractor 200 and engaged to pull the patient's flesh in a direction typically orthogonal to the force exerted by the prongs 205, 210. The first prong 205 and second prong 210 can be moved freely and independently without a requirement to move the respective prong. Each prong 205, 210 contains a respective proximal end 213 and distal end 214. A hinge assembly 215 located about midway between the ends 231, 214 pivotably connects the prongs 205, 210.

The distance between the ends 213, 214, of the prongs 205, 210 can be locked or defined by engaging a multi-position locking mechanism 220. The multi-position locking mechanism 220 has two parts, a locking ratchet 221 connected to the proximal end 213 of one respective prong 205, 210 and a receiving portion 225 connected to the proximal end 213 of the other respective prong 210, 205. The locking ratchet 221 is typically unitary with the first prong 205 and the receiving portion is typically unitary with the second prong 210. Pressure can be applied to a tab 223 extending from the locking ratchet 221 for quick release of the locking mechanism 220 (disengaging the portions 221, 225) so that the distance between the prongs 205, 210 can be adjusted. Once the proper distance is determined, the locking ratchet 221 is securely placed in the grooves or teeth of the receiving portion 225 of the locking mechanism 220. Locking the first prong 205 and the second prong 210 together at the proximal end 213 minimizes unnecessary and unwanted relative movement of the prongs 205, 210 relative one another. The proximal end 213 of each respective prong 205, 210 is typically knurled 235 for ease of gripping.

The hinge assembly 215 may be unitarily formed with the prongs 205, 210 as a single unitary piece having an aperture 237 through which a pin 240 may be inserted, or a first apertured hinge portion 250A may extend from one prong 205, 210 and a second hinge portion 250B may extend from the opposite prong 210, 205 with a in 240 extending therefrom for engaging the aperture 237. The placement of the center retractor 211 is adjustable by inserting a hinge pin 240 into one of the plurality of insertion holes 212 typically located along the centerline of the center retractor 211. Engaging the hinge pin 240 locks the center retractor 211 in place relative to the retractor 200. Blades 270 typically extend from the respective distal end 214 of the three prongs 205, 210, 211. These blades 270 are typically about one centimeter in length; however, in one embodiment the blades can be extended to four centimeters or longer. The extra length of the extendable blades 270 provides the surgeon with greater control over surgery. Blades 270 typically include a plurality of serrations or fingers 271 extending therefrom, which may curve away from the retractor 200.

The retractor typically includes a titled handle 230 that tilts at approximately 15 from the hinge 215 relative the remainder of the retractor 200 degrees to provide for maximum comfort and ease of use. As with previous embodiments, retractor 200 is typically formed from radiolucent medical grade plastic.

In operation, the distal ends 214 of prongs 205, 210 are first pressed together and are inserted far enough into the wound or incision such that the blades 270 engage tissue on either side of the wound. The pressure holding the prongs 205, 210 together is then released to allow the prongs 205, 210 to exert a spring force against the tissue, urging the wound open. The locking ratchet 220 is engaged to maintain the urging force. The retractor 200 may then be left in place to hold the wound open. Center retractor 211 may be engaged to further open the wound or incision, and lockingly engaged to center pin 240 of retractor 200.

Once the wound is no longer desired to be held open, the center retractor 211 may be disengaged, the locking ratchet disengaged, and the prongs removed from the wound/incision, typically by urging prongs 205, 210 toward one another, and the retractor 200 is removed from the wound. The retractor 200 is then disposed of as medical waste, although the retractor 200 may be sterilized and reused if so desired. X-rays made during the procedure will not be impeded or obstructed by the plastic retractor, making the retractor 200 attractive for procedures on the carotid, thrombectomies, embolectomies, pacemaker implantation, and the like.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

What is claimed is:

1. A disposable device for tissue retraction, comprising:
   a first and second elongated curved members, each having respective proximal and distal ends;
   a hinge pivotably connecting the first and second elongated curved members, wherein the first and second elongated curved members curve away from one another;
   a first blade extending from the distal end of the first elongated curved member;

a second blade extending from the distal end of the second elongated curved member;

a gripping portion extending along the each of the proximal ends of the first and second elongated curved members;

a first latching portion extending from the proximal end of the first elongated curved member;

a second latching portion extending from the proximal end of the second elongated curved member; and a third bladed elongated member lockingly engageable to the hinge;

wherein the first and second latching portions are lockingly engageable;

wherein the gripping portions extend along the proximal end of the first and second elongated curved members between the hinge and the first and second latching portions;

wherein the device is made of a generally electrically insulating nonmagnetic radiolucent material.

2. The device of claim 1, wherein the device is made of nonporous medical grade thermoplastic resin.

3. The device of claim 1, wherein a plurality of fingers extend from each respective blade.

4. The device in claim 3 wherein each finger is curved away from the retractor.

5. The disposable device for tissue retraction of claim 1, wherein the gripping portions are knurled surfaces.

6. The disposable device for tissue retraction of claim 1, wherein the hinge and the distal ends of the first and second elongated curved members are coplanar; and wherein the gripping portions are non-coplanar with the hinge and the distal ends of the first and second elongated curved members.

7. The disposable device for tissue retraction of claim 1, wherein the gripping portions are disposed at 15 degrees from coplanar with the hinge and the distal ends of the first and second elongated curved members.

8. A method for retracting tissue comprising:
a) moving distal ends of respective first and second unitary prongs of a thermoplastic resin retractor together by compressing gripping portions on proximal ends of said first and second unitary prongs, wherein the respective first and second unitary prongs are pivotably connected at a hinge;
b) inserting the distal ends into an incision;
c) allowing the distal ends to exert a first urging force away from one another on the incision;
d) locking the distal ends in position with a locking mechanism;
e) unlocking the distal ends;
f) removing the retractor from the incision; and
g) discarding the retractor;
wherein the first and second prongs are connected by a hinge and curve away from one another;
wherein the gripping portions are disposed between the locking mechanism and the hinge; and
wherein the distal ends terminate in respective toothed blades.

9. The method of claim 8 and further comprising:
h) after c) and before g), x-ray imaging through the retractor.

10. The method of claim 8 and further comprising:
i) after c) and before e), engaging a third prong to the latch for retracting tissue orthogonally relative to the respective distal ends.

11. The method of claim 8 and further comprising:
j) before a), disinfecting the retractor with ethylene oxide.

12. The method of claim 8 and further comprising:
k) before d), engaging a third member into the incision;
l) Exerting a second urging force orthogonal to the first urging force on the incision; and
m) operationally connecting the third member to the hinge.

* * * * *

UNITED STATES PATENT AND TRADEMARK OFFICE
CERTIFICATE OF CORRECTION

PATENT NO. : 12,011,150 B2  
APPLICATION NO. : 16/906338  
DATED : June 18, 2024  
INVENTOR(S) : Eric McCormick et al.

Page 1 of 1

It is certified that error appears in the above-identified patent and that said Letters Patent is hereby corrected as shown below:

On the Title Page

Item (12) delete "McCormick" and insert --McCormick et al.--

Item (72) Under Inventor Information, an additional inventor should be added to read --Steven S Maves, located at 10050 Deer Run Circle, Fishers, IN 46037--

Signed and Sealed this  
First Day of April, 2025

Coke Morgan Stewart  
*Acting Director of the United States Patent and Trademark Office*